(12) United States Patent
Shanks et al.

(10) Patent No.: US 12,258,639 B2
(45) Date of Patent: Mar. 25, 2025

(54) CROSS-ASSEMBLY PHAGE DNA SEQUENCES, PRIMERS AND PROBES FOR PCR-BASED IDENTIFICATION OF HUMAN FECAL POLLUTION SOURCES

(71) Applicants: Government of the United States as Represented by the Administrator of the U.S. Environmental Protection Agency, Washington, DC (US); University of Pittsburgh—Of the Commonwealth System of Higher Education, Pittsburgh, PA (US)

(72) Inventors: Orin C. Shanks, Lebanon, OH (US); Kyle J. Bibby, Granger, IN (US); Elyse Stachler, Pittsburgh, PA (US)

(73) Assignees: GOVERNMENT OF THE UNITED STATES AS REPRESENTED BY THE ADMINISTRATOR OF THE U.S. ENVIRONMENTAL PROTECTION AGENCY, Washington, DC (US); University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1046 days.

(21) Appl. No.: 17/201,403

(22) Filed: Mar. 15, 2021

(65) Prior Publication Data
US 2021/0222263 A1    Jul. 22, 2021

Related U.S. Application Data

(63) Continuation-in-part of application No. 15/530,122, filed on Dec. 5, 2016, now abandoned.

(60) Provisional application No. 62/386,532, filed on Dec. 4, 2015.

(51) Int. Cl.
| | | |
|---|---|---|
| C12Q 1/68 | (2018.01) | |
| C07H 21/04 | (2006.01) | |
| C12Q 1/689 | (2018.01) | |
| C12Q 1/70 | (2006.01) | |

(52) U.S. Cl.
CPC ............ *C12Q 1/701* (2013.01); *C12Q 1/689* (2013.01)

(58) Field of Classification Search
None
See application file for complete search history.

(56) References Cited

U.S. PATENT DOCUMENTS

2007/0122831 A1 * 5/2007 Bachoon ............... C12Q 1/689
435/6.15

OTHER PUBLICATIONS

Stachler et al. (Environ Sci Technol Lett. vol. 1, pp. 405-409, 2014). (Year: 2014).*

* cited by examiner

*Primary Examiner* — Jeanine A Goldberg
(74) *Attorney, Agent, or Firm* — Stein IP, LLC

(57) ABSTRACT

Methods and reagents are used to determine the presence of human fecal contamination. These relate to detection of human crAssphage, a bacteriophage present in *Bacteroides*.

2 Claims, 4 Drawing Sheets
Specification includes a Sequence Listing.

CROSS-ASSEMBLY PHAGE DNA SEQUENCES, PRIMERS AND PROBES FOR PCR-BASED IDENTIFICATION OF HUMAN FECAL POLLUTION SOURCES

CROSS-REFERENCE TO RELATED APPLICATIONS

This application is a continuation-in-part of U.S. application Ser. No. 15/530,122, filed Dec. 5, 2016, which claims priority of U.S. Provisional Application Ser. No. 62/386,532, filed Dec. 4, 2015, the entire contents of all of which are hereby incorporated by reference.

GOVERNMENT INTEREST

This invention was made with government support from the Environmental Protection Agency. The United States government has certain rights to this invention.

SEQUENCE LISTING

The instant application contains a Sequence Listing which has been submitted electronically in ASCII format and is hereby incorporated by reference in its entirety. Said ASCII copy, created on Dec. 1, 2020, is named 0075_1014_SL.TXT and is 9,777 bytes in size.

FIELD OF THE INVENTION

The present invention relates to methods and reagents for assaying a sample for the presence of fecal contamination from humans.

BACKGROUND OF THE INVENTION

Much human disease has been transmitted via fecal contaminated water. Often disease-causing bacteria and viruses found in feces are the causative agent. Testing for the presence of indicator bacteria typically found in and transmitted in feces is a well-established approach and is presumptive of fecal contamination in a water sample. The water, food, objects and environmental samples so contaminated are presumably unsafe for human consumption and contact.

Most current health, safety and regulatory methods used to assess water and food quality rely on measuring the levels of culturable indicator bacteria of fecal contamination, such as enterococci and *Escherichia coli*. These act as a proxy for pathogenic viruses and bacteria potentially present in feces as well. These general fecal indicators are shed in the fecal waste of most animals, and as a result, do not provide information on the occurrence of a particular source of fecal pollution. Fecal source information is important because different animal groups (e.g. human, cattle, birds, etc) can harbor different pathogens resulting in variable levels of public health risk when contaminating recreational waters or foods. In addition, fecal source information can help communities develop focused mitigation plans to remedy a situation, such as repairing a faulty sewage treatment plant.

Multiple approaches have been attempted to determine sources of fecal contamination in the environment. One technique is a PCR-based method that identifies human fecal pollution by targeting bacterial 16S rRNA gene sequences from fecal *Bacteroides* (Bernard and Field, AEM 66:4571-4574, 2000). However, this approach targets fecal bacteria rather than virus microorganisms. The present invention was developed to produce a fast, sensitive and specific assay for human fecal contamination utilizing a viral indicator.

Previously applicants have developed assays to distinguish bacterial strains from various animal species for fecal contamination detection. For example, U.S. Pat. Nos. 8,574,839, 8,058,000 and 7,572,584.

The Cross-Assembly phage (crAssphage) was first described by Dutilh, B. E., Cassman, N., McNair, K., Sanchez, S. E., Silva, G. G., Boling, L. & Edwards, R. A. (2014). This highly abundant bacteriophage was discovered in the unknown sequences of human fecal metagenomes. *Nature communications,* 5 as an approximately 97 kbp double stranded DNA circular genome discovered by assembly of sequence reads from a human fecal metagenome. Since the genome was derived from a population metagenomic sequence reads from the feces of multiple human individuals, the genome represents a consensus genome of a viral quasispecies. They report 80 predicted protein coding genes, two-thirds of which had no predicted function, demonstrating why the phage had not been previously discovered. Co-occurrence profiling predicted a bacterial *Bacteroides* host (i.e. the crAssphage virus may infect *Bacteroides* sp. bacteria in human feces). They also reported that the genome was highly prevalent in human fecal samples and sewage.

Based on the information in this paper, an initial metagenome evaluation was completed in Stachler, E., & Bibby, K. (2014) Metagenomic evaluation of the highly abundant human gut bacteriophage crAssphage for source tracking of human fecal pollution *Environmental Science & Technology Letters,* 1(10), 405-409. In this preliminary study, 86 metagenomes available to the public from different environments were evaluated for the presence of crAssphage by mapping sequence reads against the consensus metagenome. The crAssphage metagenome was found to be abundant in sewage samples from the U. S. and Europe while being less abundant in sewage samples from Africa and Asia. In addition, crAssphage was found to be relatively absent in samples from other animals, with the exception of one bat guano sample. Upon further inspection it was found that nearly half of the sequence reads mapping from the bat metagenome mapped to a single open reading frame (ORF) of the crAssphage genome. In addition, sewage metagenome reads from the U. S. and Europe were mapped against other known viral genomes previously suggested as human-associated fecal source identification genetic markers, showing that crAssphage is significantly more abundant than other known viruses.

Despite the initial screening of the crAssphage metagenome, many challenges remained for the development of a crAssphage human-associated genetic marker for fecal source identification applications. First, since the crAssphage metagenome is a consensus sequence, it may include errors that lead to unsuitable genetic markers. In addition, there was no laboratory data confirming the animal host range (i.e. only found in human feces), geographic stability, nor detection in an environmental sample known to be contaminated with human waste. Furthermore, with little more than theoretical data, the actual sensitivity and specificity of any crAssphage genetic marker in environmental samples remained unknown making it impossible to develop a human fecal source identification assay with the information reported in this study.

SUMMARY OF THE INVENTION

It is an object of the present invention to identify a human-associated genetic region of the crAssphage metagenome.

It is a further object of the present invention to provide methods for identifying said human-associated crAssphage genetic marker in environmental samples that harbor human fecal waste.

It is still another object of the present invention to provide DNA primers and probes which can specifically hybridize to and allow determination of the presence of the human-associated-region of the crAssphage metagenome.

The present invention performs the assay functions for two genetic regions of the crAssphage metagenome that are strongly associated with human fecal waste. The presence of the sequences in these two regions may be determined by a variety of standard molecular biology techniques on crAssphage containing samples.

DETAILED DESCRIPTION OF THE INVENTION

Definitions

Figure 1:
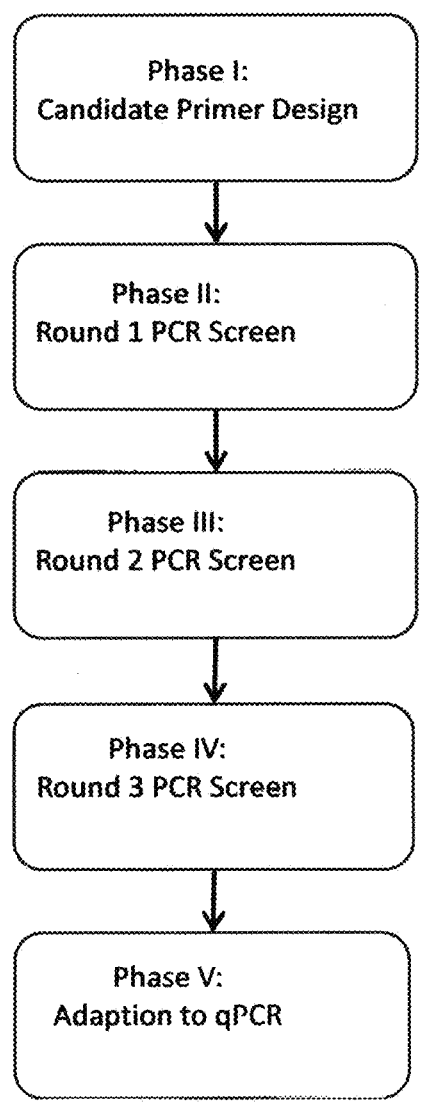
FIG. 1 Illustrates the stages of method development for human-associated fecal source identification crAssphage technology.

The crAssphage metagenome of the present invention has been described previously. The listed sequence is a metagenomic sequence derived from databases of human fecal DNA. The sequence numbering in the crAssphage metagenome is a consensus and the sequence numbering may vary slightly from sequenced true biological samples. Thus, the sequence numbering is provided for convenience and ease of understanding rather than a definition. Also, crAssphage appears to be a bacteriophage and is discussed herein as if it is due to its potential association with *Bacteroides*. However, this has yet to be proved conclusively and the term should be viewed as a convenience for ease of understanding only.

"Human specific region" refers to sequences within the crAssphage metagenome that are highly associated with human fecal waste, but not other pollution sources (i.e. not human). Slight overlap with unusual animal sources of fecal contamination, such as the odd result with certain bat fecal samples, are still considered "human specific" for the purposes of the present invention.

The present disclosure describes several potentially human-associated crAssphage genetic regions provided in the Table 3 below. More preferred are laboratory confirmed human-associated regions of crAssphage listed in Tables 4 and 5. Human-specific regions of particular interest are the regions containing any part of the genomic region of crAssphage amplified by respective PCR primers. A human-specific region may encompass the entire amplified region between and including the primers or it may include regions outside these sequences provided that it at least partially overlaps the region defined by the PCR primers described above and below.

Alternatively, the human-specific region may be defined based on amplified regions which are NOT human-specific. In the examples below, a large number of PCR amplified crAssphage genetic regions were tested. While many were not human-specific, untested regions between the tested regions may also be human-specific. Of particular interest are untested regions adjacent to suspected human-specific regions. Regardless, any region determined as not human-specific by the methods in the examples are considered not human-specific.

Reagents used in the assay of the present invention include primers, probes, and/or other oligonucleotides. These may be directly labeled, indirectly labeled or labeled and/or stained after hybridization. Many nucleotide labeling techniques are known per se. Likewise, a number of suitable labeling techniques are well known per se, such as fluorescent, quenching, enzyme, ligand, etc. The label may indicate either the presence or absence of hybridization of the primer(s) or probe(s), as long as it is sufficiently detectable to answer the question of whether the human-specific genetic region(s) of crAssphage are present in a sample. Techniques for using such a primer or probe in a variety of different assay formats are well known per se. For example, in the examples below, both end-point PCR and qPCR have been used. A real-time PCR, dPCR, ddPCR, RT-PCR and other known techniques may be used also. Primer extension products may be determined by unrelated techniques such as by mass spectrometry. Further examples include long probes to the human-specific region wherein the probe(s) may be labeled before or after hybridization. In short, any standard molecular biology method for detecting a particular sequence may be used in the present invention to detect the presence or absence of human-specific region(s) in crAssphage.

Hybridization or annealing of a primer or probe is preferably completely complementary. However, a slight non-complementarity approach may be tolerable to account for random mutations and sequence variations in different human crAssphage genomes.

CrAssphage is very abundant in fecal samples both in quantity and in its widespread locations around the world. Thus, most conventional nucleotide-based assays should not have an issue with sensitivity. An extremely dilute sample may offer challenges with sensitivity, but that is a sampling issue rather than an assay problem.

The sample suspected of containing human-specific crAssphage may be from any natural or artificial source that could possibly be exposed to human feces. Examples include, environmental samples of water, soil, air, ground water, vegetation, and surface waters. Artificial sources include wastewater, surface run-off, aerosols, food products, feed products, fiber products, manufactured goods of all kinds, but especially pharmaceuticals, medical devices, medicaments, door knobs, handrails, and anything else that can contact a human body. The sample may be from a person (external or internal) or laboratory sample such as a culture. This data suggests that the identified crAssphage genetic regions could be highly specific and sensitive human fecal source identification indicators. Several regions of the crAssphage metagenome were identified by manual inspection to be highly abundant across human metagenome samples. These regions were searched for crAssphage specific primers using PrimerBLAST and several regions were reported for being ideal for technology development (crAssphage genome bp positions: 1770-1870, 78100-78270, 83860-83970, 88370-88470, 90120-90280, and 93160-93340).

Figure 2:
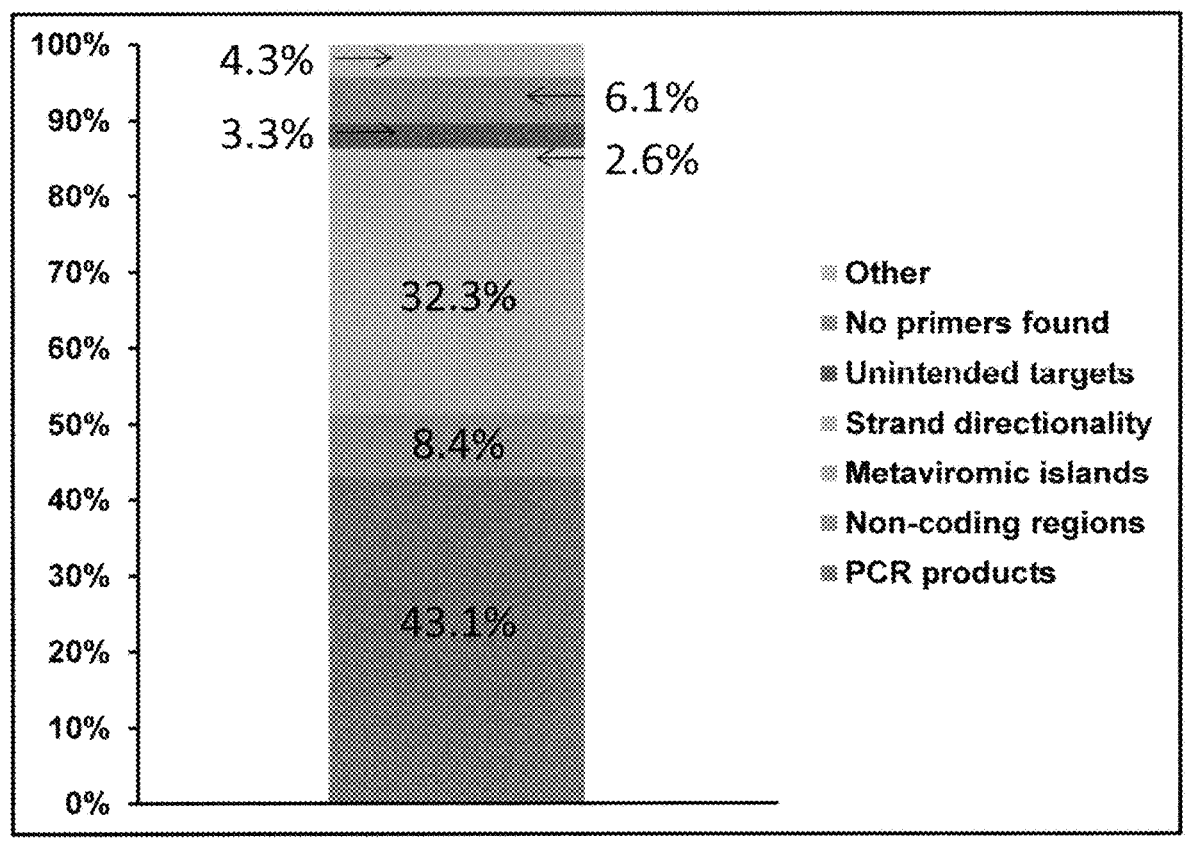
FIG. 2 Map is a representation of the crAssphage metagenome. The outermost track represents the open reading frames on the forward and reverse strand of the crAssphage metagenome. The middle track represents the areas of the crAssphage metagenome that were eliminated from primer design including noncoding regions, metaviromic islands, modular junction areas, non-target sequence homology, and regions unsuitable for primer design. The innermost track represents the genetic loci of the 384 end-point primer pairs designed in this study and their amplification products.

In order to identify candidate crAssphage primer sets, suitable for a human-specific fecal source identification technology a multistep strategy was employed (FIG. 1). In Phase I, the entire crAssphage genome was considered for the design of candidate primer sets and tested in silica using PrimerBLAST. Based on in silica results, primer sets were designed to cover the majority of the crAssphage metagenome deemed suitable for technology development based on a series of selection criteria (FIG. 2). Phase I included all regions of the crAssphage metagenome, not just the regions previously reported as ideal in the previous Stachler et al. study. A laboratory-based "shotgun" strategy was employed because the reported crAssphage consensus metagenome sequence likely harbors large amounts of genetic variation from one individual to another, which could be problematic for identifying suitable genetic regions in human waste mixed population samples such as sewage. In addition, very little is known about the nucleotide conservation in predicted gene encoding regions of the reported putative crAssphage metagenome.

After identification of probable human-specific genetic regions and the development of candidate primer sets, three stages of end-point PCR testing were conducted to identify the most suitable human-specific crAssphage genetic regions for a human fecal source identification technology (Phase II, III, and IV). The details for each Phase are detailed below. Candidate primer sets that passed all end-point PCR screens were then adapted to a qPCR technology in order to develop a quantitative technology appropriate for human fecal source identification applications (Phase V).

The following non-limiting example is provided to illustrate the present invention.

Example

Phase I: End-Point PCR Candidate Primer Set Design

The crAssphage metapopulation consensus genome of viral quasispecies was used as a template for candidate primer design to develop a human-specific fecal source identification technology. PrimerBLAST was used to design candidate primers with default parameters except product length was restricted to a range of 90 and 180 bps. When multiple primer pairs were suggested for a particular region, primer selection was based on optimizing the 3' end specificity, including 2-3 C or G for the GC clamp, looking for primers with higher $T_m$ and similar $T_m$ within the pair, higher GC content, and eliminating self-complementarity. Eligible genetic regions for candidate end-point PCR primer design were selected based on a predefined set of criteria including:

(1) Non-coding regions: Only predicted open reading frames (ORFs) were targeted because these regions often exhibit a higher degree of nucleotide conservation compared to noncoding regions.

(2) Metaviromic islands: Metaviromic islands are "genomic regions in prokaryotic genomes that under-recruit from metagenomes where most of the same genome recruits at close to 100% identity over most of its length" Mizuno, C. M., Ghai, R., & Rodriguez-Valera, F. (2014). Evidence for metaviromic islands in marine phages. Frontiers in microbiology, 5. Regions reported as metaviromic islands were excluded to help ensure candidate primer sets target stable genetic regions less likely to be involved in recombination events or harbor random mutations[1].

(3) Strand directionality: The putative crAssphage genome exhibits a change in strand directionality resulting in two main blocks of ORFs. The areas where the strand changes direction were eliminated because they are typically areas with high base composition variability and often the site of recombination events.

(4) Unintended targets: Regions with a high mapped read percentage to sequences originating from non-human sources were eliminated. For example, ORF00045 was excluded due to homology with bat virome metagenomic sequences. Stachler, E., & Bibby, K. (2014). Metagenomic evaluation of the highly abundant human gut bacteriophage CrAssphage for source tracking of human fecal pollution. *Environmental Science & Technology Letters,* 1(10), 405-409. In silica predictions based on PrimerBLAST tests of the non-redundant nucleotide database (May-June 2015) were used to identify sequences closely associated with crAssphage or clone sequences from human gut metagenome libraries.

(5) No primers found: Regions with insufficient base pair composition to design optimal primer pairs were eliminated based on PrimerBLAST default parameters for primer design.

Results:

In total, 384 candidate primer sets were designed targeting the crAssphage metapopulation consensus genome of viral quasispecies. All candidate primer sets are available upon request. During selection, 45,940 bp were found to be eligible for primer design. The 384 primer pairs and their products represent 41,794 bp, representing 91% coverage of the eligible region. FIG. 2 shows a map of the entire crAssphage genome, as well as regions eliminated based on selection criteria described above. Of the 384 primer pairs, the following regions predicted to be ideal from the previous study[2]

Phase II: Round 1 PCR Screen

Round 1 was designed to identify candidate primer sets that exclusively amplify human sewage without eliciting false positive detections to select non-target animals. Testing was conducted using two composites including (1) raw sewage and (2) non-target animals (pig, cow, dog, and goose).

Fecal Library Preparation:

Composite DNA samples were made to test the primer pairs in the first round of testing. Sewage samples were collected from three different sites in Cincinnati, Ohio DNA was extracted using the QIAamp DNA Blood Maxi Kit substituting Buffer AVL for Buffer AL. The samples were pooled and the composite was diluted to 0.5 ng/µL for a total of 1 ng/reaction. For the non-target animal composite, DNA was extracted from animal fecal samples using a modified procedure of the GeneRite DNA-EZ Kit. Nine individual samples were used for each of the four animal groups including pig, cow, dog, and goose. Samples were pooled and the composite was diluted to 2 ng/µL for a total of 4 ng/reaction (1 ng/reaction of DNA from each animal group). Each candidate primer pair was subjected to six reactions, duplicates each of the sewage composite (1 ng/reaction), the non-target animal composite (4 ng/reaction), and no template controls.

PCR Amplification Conditions:

Amplification conditions for PCR screening are described in Table 1. All end-point PCR reactions were run on a Tetrad 2 thermal cycler (BioRad Laboratories) under the following conditions: 94° C. for 5 min and 40 cycles of 40 s at 94° C., 1 min at 57° C., and 30 s at 72° C.

TABLE 1

Reaction composition for end-point PCR amplification.

| Reagent | Reaction Concentration | Volume per reaction (µL) |
| --- | --- | --- |
| Takara ExTaq | 0.625 U | 0.125 |
| Ex Taq PCR Buffer | 1X | 2.5 |
| dNTPs | 200 µM each | 2 |
| Primers | 100 nM | 1 |
| BSA | 4 ng | 0.4 |
| Water | — | 16.975 |
| DNA | 1-5 ng | — |

Figure 3:
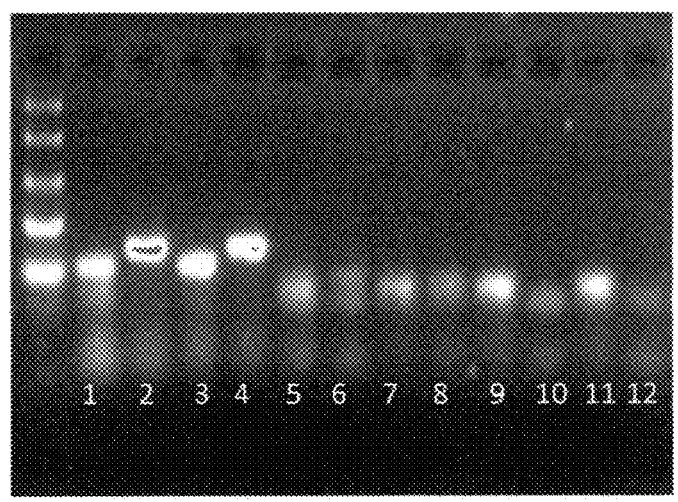
FIG. 3 is an example gel from Round 1 testing. Pictured are PCR products from primer sets crAss055 and crAss056. For primer set crAss055 wells 1 and 3: sewage composite, wells 5 and 7: non-target animal composite, wells 9 and 11: no template controls. For primer crAss056 wells 2 and 4: sewage composite, wells 6 and 8: non-target animal composite, wells 10 and 12: no template controls. Ladder shown ranges from 100 bp to 2 kbp.

Results:

PCR products were visualized by electrophoresis on 2.0% lithium borate buffer gels using a UVP gel imager. Refer to FIG. 3 for an example. Candidate primer sets were evaluated based on the following criteria:

Positive detection in sewage composite, defined as a clear band of expected product size in at least one of two sewage replicate reactions.

Negative detection in non-target animal composite, defined as an absence of band of expected product size in non-target animal replicate reactions.

Negative detection in no template controls, defined as absence of band of expected product size in either NTC reaction.

Absence of spurious bands, defined as product bands of sizes other than the expected product found in any reaction.

Minimal primer dimerization product, defined as evidence of amplification smaller than the expected product size caused from the primers self-amplifying.

Example Gel from Round 1 (FIG. 3). Pictured are PCR products from primer sets crAss055 and crAss056. For primer set crAss055 wells 1 and 3: sewage composite, wells 5 and 7: non-target animal composite, wells 9 and 11: no template controls. For primer crAss056 wells 2 and 4: sewage composite, wells 6 and 8: non-target animal composite, wells 10 and 12: no template controls. Ladder shown ranges from 100 bp to 2 kbp.

Results of Round 1 screening are listed in Table 2. In summary, only 57 candidate primer sets were eligible for Round 2 testing (complete data set available upon request). Of the 384 primers, 31.5% failed to detect the sewage composite. This included a large region of the genome where no primers worked (crAssphage genome locus 25607 to 43723 bp) suggesting that this region may be present at too low of a concentration to detect, represented a region of genetic variation between different quasispecies, or indicates errors in the reported crAssphage consensus genome. Regardless, data indicates that this region is not suitable for human fecal source identification technology development. In addition, 6.8% of primers tested showed false positives, 2.6% had spurious bands in sewage composite, and 1.3% had spurious bands in non-target animal composite, eliminating them from further testing. Of all the primer sets tested, only one had a positive NTC. The rest of the primers were eliminated from further testing due to presence of undesirable primer dimerization amplification products.

TABLE 2

Results of Round 1 Testing

| Selection Criteria | No. of primer sets |
| --- | --- |
| Positive Products | 254 |
| No Product | 121 |
| Spurious Bands in Sewage | 10 |
| Spurious Bands in Animals | 5 |
| False Positives | 26 |
| Positive NTC | 1 |
| Primer Dimerization product | 166 |

Phase III: Round 2 PCR Screen

Round 2 was designed to test candidate primer set sensitivity to sewage and increase test concentrations of non-target animals to more rigorously assess specificity. For sensitivity testing, three dilutions were prepared from the sewage composite used in Round 1 including test concentrations of 0.1 ng/reaction, 0.01 ng/reaction, and 0.001 ng/reaction. For specificity testing, each non-target animal group was tested individually at a test concentration of 5 ng/reaction. The same reaction composition and thermal cycling conditions for Round 1 were used.

Results:

PCR products were visualized by electrophoresis on 2.0% lithium borate buffer gels using a UVP gel imager. Refer to FIG. 3 for example. Candidate primer sets were evaluated based on the following criteria:

Positive detection in each sewage composite dilution defined as a clear band of expected product size in at least one of two sewage composite replicate reactions.

Negative detection in non-target animal composite defined as an absence of band of expected product size in either replicate reaction.

Negative detection in no template controls defined as the absence of band of expected product size in either reaction.

Absence of spurious bands defined as product bands of sizes other than the expected product size found in any reaction.

Minimal primer dimerization product defined as evidence of amplification smaller than the expected product size caused from the primers self-amplifying.

Figure 4:
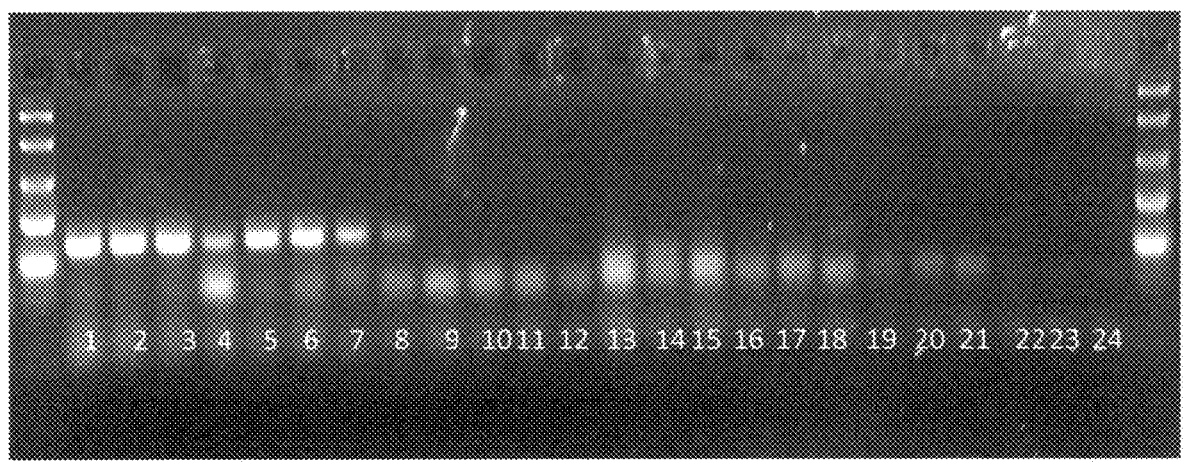
FIG. 4 shows an example gel from Round 2 Testing. Pictured are results for Primer crAssphage064. The wells are set up as follows: wells 1-3 triplicate sewage composite 0.1 ng/reaction, wells 4-6 triplicate sewage composite 0.01 ng/reaction, wells 7-9 triplicate sewage composite 0.001 ng/reaction, wells 10-12 triplicate NTC, wells 13-15 triplicate pig composite, wells 16-18 triplicate cow composite, wells 19-21 triplicate dog composite, wells 22-24 triplicate goose composite. Ladder shown ranges from 100 bp to 2 kbp.

In total, six candidate primer sets passed all selection criteria and were deemed eligible for Round 3 testing. FIG. 4 shows results from the crAss056 primer set. An additional 10 candidate primer sets passed all but one criteria and are identified as "alternates". These candidate primer sets may not have performed perfectly in Round 2, but performed well enough that they could be potentially optimized to yield high performance human fecal source identification technologies. It is important to note that none of the primers passing to Round 3 are located in any of the areas previously identified along the crAssphage genome to be ideal for marker development[2]. This indicates that the previously reported in silica approach was insufficient for determining the most suitable crAssphage genetic regions for human-specific fecal source identification technology development.

Example: Gel from Round 2 Testing. Pictured in FIG. 4 are results for Primer crAssphage064. The wells are set up as follows: wells 1-3 triplicate sewage composite 0.1 ng/reaction, wells 4-6 triplicate sewage composite 0.01 ng/reaction, wells 7-9 triplicate sewage composite 0.001 ng/reaction, wells 10-12 triplicate NTC, wells 13-15 triplicate pig composite, wells 16-18 triplicate cow composite, wells 19-21 triplicate dog composite, wells 22-24 triplicate goose composite. Ladder shown ranges from 100 bp to 2 kbp.

TABLE 3

Candidate primer sets passing Round 2 testing.

| Primer Set | Primer | Sequence | SEQ ID NO: | Genome Region |
|---|---|---|---|---|
| Selected: | | | | |
| crAss028 | crAss028-For | TGACTCTAGTCAGCTTCCACC | 3 | 7450-7470 |
|  | crAss028-Rev | TCTCCTTGTCGTACAACTTCTTT | 4 | 7548-7526 |
| crAss056 | crAss056-For | GCTGAACAAACTGCTAATGCAGA | 5 | 14712-14734 |
|  | crAss056-Rev | TCAAGATGACCAATAAACAAGCCA | 6 | 14860-14837 |
| crAss064 | crAss064-For | TGCTGCTGCAACTGTACTCT | 7 | 16038-16057 |
|  | crAss064-Rev | CGTTGTTTTCATCTTTATCTTGTCC | 8 | 16177-16153 |
| crAss301 | crAss301-For | AGCCGAATTAATTTCCTGACGA | 9 | 82338-82359 |
|  | crAss301-Rev | TGCTCTTATTAATTCTGACCCATCT | 10 | 82437-82413 |
| crAss303 | crAss303-For | TCTTCGGCTCTAAAACGAAGATAA | 11 | 82630-82653 |
|  | crAss303-Rev | GGTCTTGCTCCTAATAATGAAAACT | 12 | 82778-82754 |
| crAss375 | crAss375-For | AAGCAAATCAAGATTCCATCTACC | 13 | 91642-91665 |
|  | crAss375-Rev | TTTAATAGTCAGAGAGTTGCTGAAC | 14 | 91770-91746 |
| Alternates: | | | | |
| crAss016 | crAss016-For | TTCATGCAGAATGTCTAAGTCAAGA | 15 | 3556-3580 |
|  | crAss016-Rev | AAACATCATTTTCAGGGTCAACA | 16 | 3648-3626 |
| crAss238 | crAss238-For | ACAGGAAGATTACACATACCTGC | 17 | 60310-60332 |
|  | crAss238-Rev | GAAGTTCCAAAGCCAGTTAGATT | 18 | 60455-60433 |
| crAss276 | crAss276-For | TGCCGCCATAGCAGATTGAA | 19 | 79232-79251 |
|  | crAss276-Rev | TCTTATGGCACAATATGGACTTGA | 20 | 79343-79320 |
| crAss294 | crAss294-For | GCCATTATAACTAACTTGAAAGCCT | 21 | 81604-81628 |
|  | crAss294-Rev | GGTACTGTTAACGGCGGAGA | 22 | 81720-81701 |
| crAss300 | crAss300-For | CAGTATCCATAGCCATACCGTT | 23 | 82226-82247 |
|  | crAss300-Rev | AGCGTCTTGCTAAACATCGTC | 24 | 82375-82355 |
| crAss326 | crAss326-For | AGTAACAGAAACACCTACAAGTTCT | 25 | 85484-85508 |
|  | crAss326-Rev | ACGGTAATCTTATTGACGATAAAGG | 26 | 85632-85608 |
| crAss328 | crAss328-For | GTCATTCGCTTTGTCATTAGGCTT | 27 | 85706-85729 |
|  | crAss328-Rev | GTAAAACAGGGCAGTTAGATGCTG | 28 | 85854-85831 |
| crAss341 | crAss341-For | TCTTCCAAAACCAGGCAAAGT | 29 | 87413-87434 |

TABLE 3-continued

Candidate primer sets passing Round 2 testing.

| Primer Set | Primer | Sequence | SEQ ID NO: | Genome Region |
|---|---|---|---|---|
| | crAss341-Rev | TGGCTCTCGTGCTACAAGTAT | 30 | 87524-87504 |
| crAss358 | crAss358-For | TGCAACATAAGTACCGGGAAGA | 31 | 89363-89384 |
| | crAss358-Rev | AGACGTGGTAACGAAGACCC | 32 | 89479-89460 |
| crAss370 | crAss370-For | GCAGTAGCTCCATGTTCAGTAAC | 33 | 90540-90562 |
| | crAss370-Rev | TCTGCTCCTTGTTGGCAAAATC | 34 | 90679-90658 |

Phase IV: Round 3 PCR Screen

Round 3 represents the most rigorous level of testing designed to select the top performing candidate primer sets for specificity, sewage geographic distribution in the United States, environmental detection demonstration, and PCR product sequencing. The six candidate primer sets that passed Round 2 were tested (Table 3).

Specificity. Excellent specificity is the foundation of any useful microbial source tracking technology. Candidate primer sets passing Round 2 were tested against a panel of non-target animal sources. Fecal reference samples include domestic dog, pig, cattle, Canada goose, whitetail deer, horse, elk, duck, beaver, and gull. Each animal group consisted of 9 individual samples. Each sample was tested in triplicate at a 1 ng/reaction test concentration (total of 270 reactions per primer set). Resulting data was used to calculate specificity [true negatives/(true negatives+false positives)] for each candidate primer set.

U.S. Sewage Geographic Distribution. Computer analyses of United States sewage sample metagenomic libraries suggests that the crAssphage is highly abundant. Candidate primer sets passing Round 2 were tested against raw sewage samples collected from 10 different geographic locations across the United States. Each sewage preparation was tested in triplicate at 1 ng/reaction Limit of Detection (LOD$_{95}$). The limit of detection of each candidate primer set passing Round 2 was tested to characterize the lowest sewage template concentration detected in 95% of replicate samples. A composite of DNA sewage samples from 10 different geographic locations was tested at five concentrations ranging from 1 ng/reaction to 0.0001 ng/reaction. For each test concentration, 20 replicates were performed to calculate the proportion of positives. The lowest test concentration where at least 95% of replicates were positive was defined as the LOD$_{95}$.

Environmental Detection Demonstration. The ultimate goal for a crAssphage human-specific microbial source tracking technology is to detect human pollution in unknown samples. Even though a particular candidate primer set may yield a detectable PCR product in a sewage sample, the genetic target may not persist in the sample environment at detectable concentrations. To demonstrate detection in an environmental sample, each candidate primer set passing Round 2 was tested against a sewage impaired water sample collected from a local stream.

Results:

Top performing crAssphage genomic regions for human fecal pollution identification are listed in Table 4.

TABLE 4

End-Point PCR Primer Sequences

| Primer Set | Primer | Sequence 5'→3' | SEQ ID NO: | Genome Region |
|---|---|---|---|---|
| crAss056 | crAss056-For | GCTGAACAAACTGCTAATGCAGA | 5 | 14712-14734 |
| | crAss056-Rev | TCAAGATGACCAATAAACAAGCCA | 6 | 14860-14837 |
| crAss064 | crAss064-For | TGCTGCTGCAACTGTACTCT | 7 | 16038-16057 |
| | crAss064-Rev | CGTTGTTTTCATCTTTATCTTGTCC | 8 | 16177-16153 |

Phase V: Adaption to qPCR Platform

The top two performing primer sets based on results from Round 3 testing were adapted to the TaqMan qPCR technology.

A BLASTn search using the nr database identified crAssphage056 and craAssphage064 sequences encoding for hypothetical proteins of the crAssphage metagenome Orf000024 and Orf000025, respectively.

Genomic Regions Include:

crAss056 Genomic Region (14712-14860)
SEQ. ID #1
GCTGAACAAACTGCTAATGCAGAAGTACAAACTCCTAAAAAACGTAGAGG
TAGAGGTATTAATAACGATTTACGTGATGTAACTCGTAAAAAGTTTGATG
AACGTACTGATTGTAATAAAGCTAATGGCTTGTTTATTGGTCATCTTGA crAss064 Genomic Region (16030-16177)
SEQ. ID #2
TGTATAGATGCTGCTGCAACTGTACTCTCTGAAATTGTTCATAAGCAAAT
TGATATTTCTATTAAAAGTCAATTTCTATTTGTTCTTAAACATATTGCTT
ATACTTTTAGAAATATTATTTATGGACAAGATAAAGATGAAAACAACG SEQ ID NO:5 is a section of SEQ ID NO: 1 and SEQ ID NO: 7 is a section of SEQ ID NO:2. While other sections of SEQ ID NO:1 or SEQ ID NO: 2 are shown to be useful, these smaller sequences of SEQ ID 1 and 2 are preferred and would be particularly useful.

Primers and hydrolysis probes were designed using Life Technologies Primer Express Software and expert judgement (Table 5).

TABLE 5 qPCR Primer and Probe Sequences

| Primer Set | Primer | Sequence 5'→3' | SEQ ID NO: | Genome Region |
|---|---|---|---|---|
| crAss056 | crAss056_F1 | CAGAAGTACAAACTCCTAAAAAACGTAGAG | 35 | 14712-14860 |
|  | crAss056_R1 | GATGACCAATAAACAAGCCATTAGC | 36 |  |
|  | crAss056_P1 | [FAM]AATAACGATTTACGTGATGTAAC[MGB] | 37 |  |
| crAss064 | crAss064_F1 | TGTATAGATGCTGCTGCAACTGTACTC | 38 | 16030-16177 |
|  | crAss064_R1 | CGTTGTTTTCATCTTTATCTTGTCCAT | 39 |  |
|  | crAss064_P1 | [FAM]CTGAAATTGTTCATAAGCAA[MGB] | 40 |  |

In addition, a customized DNA standard was developed for calibration model generation. qPCR technologies were evaluated for calibration model performance, abundance in target and non-target samples, as well as performance in environmental water samples. Calibration model performance of qPCR assays is shown in Table 6.

TABLE 6

Calibration model performance parameters for qPCR assays.
The efficiency is defined as $E = 1-10^{(-1/slope)}$.

| Assay | Slope | Y-intercept | E | LLOQ |
|---|---|---|---|---|
| crAss056 | −3.466 | 40.91-42.41 | 0.943 | 37.73-39.27 |
| crAss064 | −3.385 | 42.63-43.80 | 0.974 | 39.35-40.69 |

Specificity and sensitivity testing were conducted with 222 individual fecal and sewage samples collected from 10 different geographic locations across the United States. Table 7 summarizes results for both end-point and qPCR crAssphage0056 and crAssphage064 assays. Specificity and sensitivity test reactions were standardized to 1 ng/reaction of total DNA. For qPCR data, only results above the lower limit of quantification (LLOQ) were scored as false positives.

TABLE 7

Sensitivity and Specificity of End-Point PCR and qPCR Assays

| Pollution Source | No. of Samples | No. of Replicates | End-point PCR | | qPCR | |
|---|---|---|---|---|---|---|
|  |  |  | crAssphage056 | crAssphage064 | crAssphage056 | crAssphage064 |
| Sewage | 10 | 30 | 28 | 27 | 27 | 27 |
| Cow | 61 | 183 | 3 | 3 | 0 | 0 |
| Dog | 41 | 123 | 6 | 9 | 3 | 3 |
| Gull | 25 | 75 | 9 | 8 | 3 | 4 |
| Horse | 20 | 60 | 2 | 1 | 0 | 0 |
| Elk | 20 | 60 | 0 | 1 | 0 | 0 |
| Chicken | 11 | 33 | 0 | 1 | 0 | 0 |
| Goose | 18 | 54 | 0 | 1 | 0 | 0 |
| Pig | 9 | 27 | 0 | 0 | 0 | 0 |
| Beaver | 8 | 24 | 0 | 0 | 0 | 0 |
| Deer | 9 | 27 | 0 | 0 | 0 | 0 |
| Sensitivity |  |  | 93.3% | 90% | 90% | 90% |
| Specificity |  |  | 97.0% | 96.4% | 99.1% | 98.9% |

*Test quantity standardized to 1 ng/reaction of total DNA

TABLE 8

Abundance of crAssphage qPCR genetic markers in sewage, non-human fecal, and polluted environmental water sample types

| Sample Type | Sample No. | crAssphage056 qPCR | crAssphage064 qPCR |
|---|---|---|---|
| Sewage | 10 of 10 | 1.49 to 3.37 $\log_{10}$ copies/rxn | 1.83 to 3.47 $\log_{10}$ copies/rxn |
| Environmental Water | 6 of 6 | 2.12 to 2.50 $\log_{10}$ copies/rxn | 2.23 to 2.55 $\log_{10}$ copies/rxn |
| Non-Human Fecal | 3 of 212 | 1.08 to 1.96 $\log_{10}$ copies/rxn | 1.15 to 2.60 $\log_{10}$ copies/rxn |

The quality of findings was verified through a series of rigorous controls. The absence of contamination was confirmed in both no template control (n=112) and extraction blank reactions (n=27). For environmental water samples, a sample processing control was included with each DNA extract. All sample processing controls demonstrated the absence of matrix interference. Amplification inhibition for all DNA extracts was monitored with internal amplification controls using HF183/BacR287 and HumM2 qPCR multiplex assays. Only 98.7% of all DNA extracts exhibited no inhibition. DNA extract with amplification inhibition (cow=2; gull=1) were discarded from the study.

To characterize the abundance of crAssphage056 and crAssphage064 human-specific genetic markers in common pollution sources, each assay was tested against a collection of 224 sewage, fecal, and environmental water samples collected from 10 different geographic locations across the United States. Table 8 summarizes the range of concentrations observed in logo copies/reaction. For fecal and sewage samples, test reactions were standardized to 1 ng/reaction of total DNA.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

All patents and references cited herein are explicitly incorporated by reference in their entirety.

What is claimed is:

1. A method for identifying human fecal material in a test sample, comprising the steps of:
   a) preparing a composition for use in a hybridization test, wherein said composition consists of the nucleotide sequence of SEQ ID NO: 1 or the complete complement of the nucleotide sequence of SEQ ID NO: 1,
   b) contacting a sample to the composition prepared in step a), then
   c) subjecting the product of step b) to a hybridization test to determine whether there is binding of a sequence in said sample to a sequence in the product of step a), wherein hybridization binding to the nucleotide sequence identified in step a) is evidence of human fecal material.

2. A method for identifying human fecal material in a test sample, comprising the steps of:
   a) preparing a composition for use in a hybridization test, wherein said composition consists of at least one of SEQ ID NO: 5 or SEQ ID NO: 6
   b) contacting a sample to the composition prepared in step a), then
   c) subjecting the product of step b) to a hybridization test to determine whether there is binding of a sequence in said sample to a sequence in the product of step a), wherein hybridization binding to the nucleotide sequence identified in step a) is evidence of human fecal material.

* * * * *

SEQUENCE LISTING

<160> NUMBER OF SEQ ID NOS: 40

<210> SEQ ID NO 1
<211> LENGTH: 149
<212> TYPE: DNA
<213> ORGANISM: Unknown
<220> FEATURE:
<223> OTHER INFORMATION: Description of Unknown:
      crAss056 Genomic Region sequence

<400> SEQUENCE: 1
gctgaacaaa ctgctaatgc agaagtacaa actcctaaaa aacgtagagg tagaggtatt      60
aataacgatt tacgtgatgt aactcgtaaa aagtttgatg aacgtactga ttgtaataaa     120
gctaatggct tgtttattgg tcatcttga                                       149

<210> SEQ ID NO 2
<211> LENGTH: 148
<212> TYPE: DNA
<213> ORGANISM: Unknown
<220> FEATURE:
<223> OTHER INFORMATION: Description of Unknown:
      crAss064 Genomic Region sequence

<400> SEQUENCE: 2
tgtatagatg ctgctgcaac tgtactctct gaaattgttc ataagcaaat tgatatttct      60
attaaaagtc aatttctatt tgttcttaaa catattgctt atacttttag aaatattatt     120
tatggacaag ataagatga aaacaacg                                         148

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgactctagt cagcttccac c                                                21

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tctccttgtc gtacaacttc ttt                                              23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctgaacaaa ctgctaatgc aga                                              23

<210> SEQ ID NO 6
<211> LENGTH: 24
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 6
tcaagatgac caataaacaa gcca                                              24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgctgctgca actgtactct                                                   20

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgttgttttc atctttatct tgtcc                                             25

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agccgaatta atttcctgac ga                                                22

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgctcttatt aattctgacc catct                                             25

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcttcggctc taaaacgaag ataa                                              24

<210> SEQ ID NO 12
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 12
ggtcttgctc ctaataatga aaact                                          25

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aagcaaatca agattccatc tacc                                           24

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tttaatagtc agagagttgc tgaac                                          25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttcatgcaga atgtctaagt caaga                                          25

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aaacatcatt ttcagggtca aca                                            23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acaggaagat tacacatacc tgc                                            23

<210> SEQ ID NO 18
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 18
gaagttccaa agccagttag att                                          23

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgccgccata gcagattgaa                                              20

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tcttatggca caatatggac ttga                                         24

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gccattataa ctaacttgaa agcct                                        25

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggtactgtta acggcggaga                                              20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cagtatccat agccataccg tt                                           22

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 24
agcgtcttgc taaacatcgt c                                              21

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agtaacagaa acacctacaa gttct                                          25

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acggtaatct tattgacgat aaagg                                          25

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtcattcgct ttgtcattag gctt                                           24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gtaaaacagg gcagttagat gctg                                           24

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tcttccaaaa ccaggcaaaa gt                                             22

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tggctctcgt gctacaagta t          21

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgcaacataa gtaccgggaa ga          22

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agacgtggta acgaagaccc          20

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcagtagctc catgttcagt aac          23

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tctgctcctt gttggcaaaa tc          22

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cagaagtaca aactcctaaa aaacgtagag          30

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 36
gatgaccaat aaacaagcca ttagc                                          25

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aataacgatt tacgtgatgt aac                                            23

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tgtatagatg ctgctgcaac tgtactc                                        27

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cgttgttttc atctttatct tgtccat                                        27

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ctgaaattgt tcataagcaa                                                20
```